US 12,064,085 B2

(12) United States Patent
Suwa

(10) Patent No.: US 12,064,085 B2
(45) Date of Patent: Aug. 20, 2024

(54) ENDOSCOPE AND METHOD OF MANUFACTURING ENDOSCOPE

(71) Applicant: OLYMPUS MEDICAL SYSTEMS CORP., Tokyo (JP)

(72) Inventor: Takahiro Suwa, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 122 days.

(21) Appl. No.: 17/592,750

(22) Filed: Feb. 4, 2022

(65) Prior Publication Data

US 2023/0248225 A1 Aug. 10, 2023

(51) Int. Cl.
*A61B 1/005* (2006.01)
*A61B 1/00* (2006.01)

(52) U.S. Cl.
CPC .......... *A61B 1/0057* (2013.01); *A61B 1/0011* (2013.01); *A61B 1/00149* (2013.01); *A61B 1/00154* (2013.01)

(58) Field of Classification Search
CPC . A61B 1/0057; A61B 1/0011; A61B 1/00149; A61B 1/00154; A61B 1/00098; A61B 1/00119; A61B 1/00128
USPC .......................................................... 600/107
See application file for complete search history.

(56) References Cited

U.S. PATENT DOCUMENTS

| | | | | |
|---|---|---|---|---|
| 2001/0044570 A1* | 11/2001 | Ouchi | ................ | A61B 1/00177 600/107 |
| 2016/0089124 A1* | 3/2016 | Morimoto | .......... | A61B 1/00098 606/205 |
| 2017/0020370 A1* | 1/2017 | Yamaya | ............. | A61B 1/00142 |
| 2018/0078121 A1* | 3/2018 | Yasuda | .............. | A61B 1/00177 |
| 2018/0116491 A1* | 5/2018 | Yamaya | ................. | A61B 90/04 |
| 2018/0317742 A1* | 11/2018 | Yamaya | ............... | A61B 1/0008 |
| 2019/0142242 A1* | 5/2019 | Yamaya | ............... | A61B 1/0011 600/101 |
| 2020/0315428 A1* | 10/2020 | Harada | ............. | A61B 1/00112 |
| 2020/0367732 A1* | 11/2020 | Yamaya | ............ | A61B 1/00098 |

FOREIGN PATENT DOCUMENTS

| | | |
|---|---|---|
| JP | 08-173376 A | 7/1996 |
| JP | 2004-267596 A | 9/2004 |
| JP | 2010-201020 A | 9/2010 |
| JP | 2018-134308 A | 8/2018 |

* cited by examiner

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

An endoscope includes: a connection member that has an attaching and detaching direction defined to be orthogonal to a central axis of a distal end rigid portion in a longitudinal direction and is engaged with a wire connection portion of a movable member; and a rigid guide including a wire insertion path that guides a pulling wire, a distal end opening of the wire insertion path being disposed on a proximal end side of the movable member. The distal end opening of the wire insertion path of the rigid guide is disposed at a position closer to the central axis of the distal end rigid portion in an attaching direction of the connection member than a position in a plane formed by a rotation trajectory of the connection member.

20 Claims, 14 Drawing Sheets

ENDOSCOPE AND METHOD OF MANUFACTURING ENDOSCOPE

BACKGROUND OF THE INVENTION

1. Field of the Invention

The present invention relates to an endoscope including a movable member such as a treatment instrument raising base (forceps elevator) that is movable by wire pulling and loosening, and a method of manufacturing the endoscope.

2. Description of Related Art

An endoscope used in the medical or industrial field has been conventionally known. In a known endoscope in these days, a treatment instrument raising base is provided at a distal end portion of an insertion portion. For example, Japanese Patent Application Laid-Open Publication No. H08-173376 discloses a configuration of such an endoscope in which a raising wire (pulling wire) is connected in a side plane direction of the treatment instrument raising base.

SUMMARY OF THE INVENTION

An endoscope according to an aspect of the present invention includes: a distal end rigid portion provided at a distal end portion of an insertion portion configured to be inserted into a subject, a movable member rotatably held to the distal end rigid portion, the movable member including a wire connection portion; a pulling wire configured to be pulled to rotate the movable member; a connection member provided at a distal end of the pulling wire, the connection member being engaged with the wire connection portion of the movable member, an attaching and detaching direction of the connection member being defined, the attaching and detaching direction being orthogonal to a center axis along a longitudinal direction of the distal end rigid portion; and a rigid guide including a wire insertion path configured to guide the pulling wire, a distal end opening of the wire insertion path being arranged on a proximal end side with respect to the movable member. The distal end opening of the wire insertion path of the rigid guide is arranged at a position closer to the center axis of the distal end rigid portion than a position in a plane formed by a rotation trajectory of the connection member that rotates with the rotation of the movable member, the center axis being on a side in an attaching direction opposite to a detaching direction in the attaching and detaching direction of the connection member.

An endoscope manufacturing method according to an aspect of the present invention includes: causing a frame member to rotatably hold a movable member; engaging a pulling wire with a connection portion for connection with the movable member, the pulling wire being configured to rotate the movable member; arranging a distal end of a path of a rigid guide on a proximal end side with respect to the movable member, the rigid guide being configured to guide the pulling wire; and causing a distal end opening of the path of the rigid guide to be positioned at a position closer to a center axis along a longitudinal axis of the frame member than a position in a plane formed by a rotation trajectory of the connection portion that rotates with the rotation of the movable member.

DETAILED DESCRIPTION OF PREFERRED EMBODIMENT

Typically, when an operation wire as a pulling member is pulled backward to raise a treatment instrument raising base as a movable member, the operation wire receives impact in a direction in which the operation wire comes off the treatment instrument raising base because there is a tension component that pulls the operation wire in a side plane direction.

In other words, the operation wire potentially comes off the treatment instrument raising base due to impact at pulling, or a defect such as an insufficient angle at which a treatment instrument is raised due to backlash potentially occurs even though the operation wire does not come off.

Thus, the present invention achieves an endoscope that prevents an operation wire from coming off a movable member such as a treatment instrument raising base due to impact at pulling and solves a defect such as backlash, and a method of manufacturing the endoscope.

An embodiment of an endoscope as an insertion instrument according to an aspect of the present invention will be described below with reference to the accompanying drawings. Note that a configuration of the present invention is not limited by the embodiment described below.

The endoscope is, for example, an oblique-viewing endoscope among ultrasound endoscopes. The endoscope is applicable to a digestive organ endoscope including a flexible insertion portion configured to be inserted into a digestive organ in an upper or lower part of a living body, as well as various kinds of what is called flexible scopes, what is called a rigid endoscope that includes a rigid insertion portion and is used for surgery.

In addition, the present invention is applicable to medical endoscopes as well as various kinds of endoscopes such as an industrial endoscope. Specifically, the present invention is a technology that is applicable to, for example, an image pickup unit and an endoscope in which a movable member such as a treatment instrument raising base is attached to a distal end portion of an insertion portion.

Note that, in the following description, the drawings are schematic, and dimensional relations between elements, ratios of elements, and the like may be different from relations and ratios in reality in some cases. The dimensional relations between elements and the ratios of elements may be also different between the drawings in some cases.

Embodiment

Figure 1:
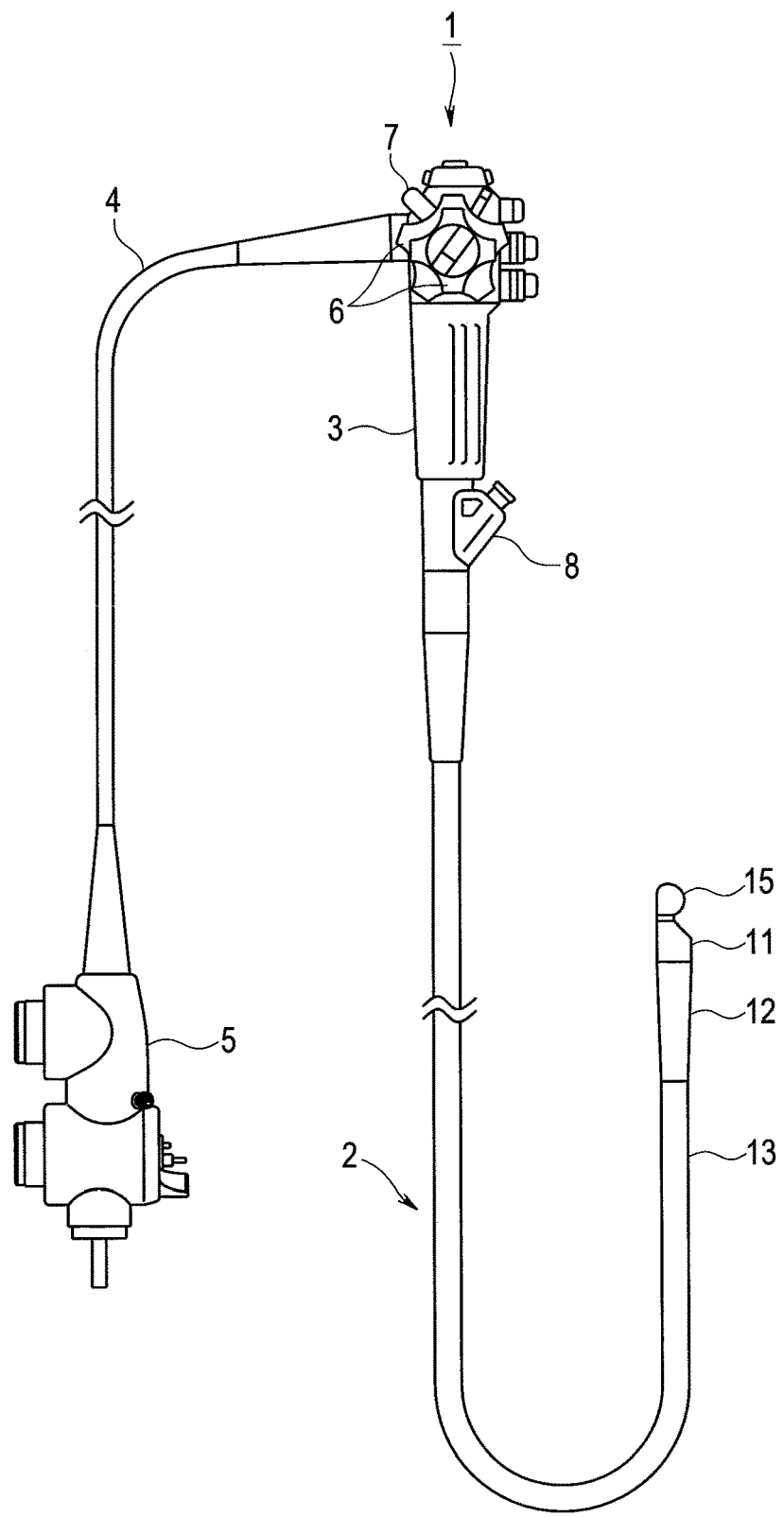
FIG. 1 is a schematic diagram illustrating a configuration of an endoscope according to an aspect of the present invention.

As illustrated in FIG. 1, an endoscope 1 as an insertion instrument according to the present embodiment includes an insertion portion 2, an operation portion 3, a universal cord 4, and an endoscope connector 5.

The insertion portion 2 includes, at the distal end thereof, elongated members such as image pickup and illumination components. The insertion portion 2 is configured to be inserted into a subject. The operation portion 3 is continuously provided on a proximal end side of the insertion portion 2. The universal cord 4 extends from a side part of the operation portion 3. The endoscope connector 5 is continuously provided with the universal cord 4. The endoscope connector 5 is connected to an observation device that controls the endoscope 1, a light source device for supplying illumination light to the endoscope 1, and the like.

The insertion portion 2 includes, sequentially from a distal end side, a distal end portion 11, a bending portion 12, and a flexible tube portion 13. The bending portion 12 can be freely bent in accordance with an operation of a bending knob 6 provided to the operation portion 3. The flexible tube portion 13 has flexibility.

The flexible tube portion 13 of the insertion portion 2 is continuously provided on the distal end side of the operation portion 3. An ultrasound transducer 15 is disposed at a distal end of the distal end portion 11 of the insertion portion 2. However, the endoscope 1 may be various kinds of endoscopes including no ultrasound transducer.

Figure 2:
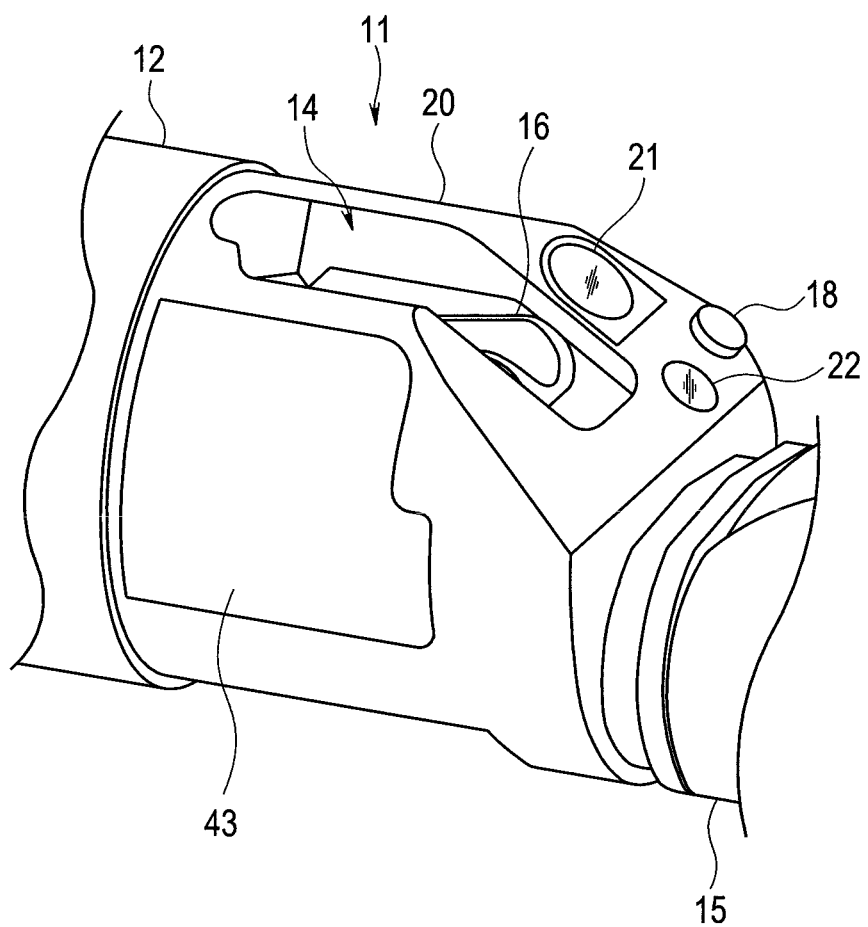
FIG. 2 is a perspective view partially illustrating a configuration of a distal end portion.

Note that the distal end portion 11 is provided with an opening 14 and provided with a treatment instrument raising base (also referred to as a forceps elevator) 16 that can change a direction in which a treatment instrument such as a forceps extends from the opening 14 (refer to FIG. 2). The distal end portion 11 is also provided with a treatment-instrument channel opening (not illustrated) communicating with the opening 14.

In the distal end portion 11, an observation window 21, an illumination window 22, and a gas-liquid feeding nozzle 18 are disposed on a slant face formed at a side part of the opening 14. Specifically, the endoscope 1 is an oblique-viewing endoscope having a visual field in a front oblique direction. Note that the endoscope 1 may be a side-viewing endoscope having a visual field in a side direction.

The operation portion 3 is provided with a forceps insertion port 8 for inserting a treatment instrument such as a forceps needle into the subject. The operation portion 3 is also provided with an operation lever 7 for operating the treatment instrument raising base 16 disposed at the distal end portion 11.

A forceps insertion path is provided inside the insertion portion 2, and the forceps insertion port 8 serves as an insertion port of a treatment-instrument channel. Thus, the endoscope 1 is an endoscope in which a treatment instrument can be inserted.

Description below is made on a configuration of the distal end portion 11 of the insertion portion 2 according to the present embodiment, mainly, a mechanism with which the treatment instrument raising base 16 is movable.

As illustrated in FIG. 2, the distal end portion 11 of the endoscope 1 is disposed at the distal end of the insertion portion 2. The distal end portion 11 includes a distal end rigid portion (also referred to as a distal end component) 20 as a frame member formed of, for example, resin or metal.

The above-described opening 14 is formed at the distal end rigid portion 20. The treatment instrument raising base 16 is positioned in the opening 14 of the distal end rigid portion 20. The treatment instrument raising base 16 contacts a treatment instrument such as a forceps and changes a direction in which the treatment instrument protrudes. The treatment instrument raising base 16 is formed of, for example, metal such as stainless steel or aluminum, or rigid material such as alloy or ceramics.

Figure 3:
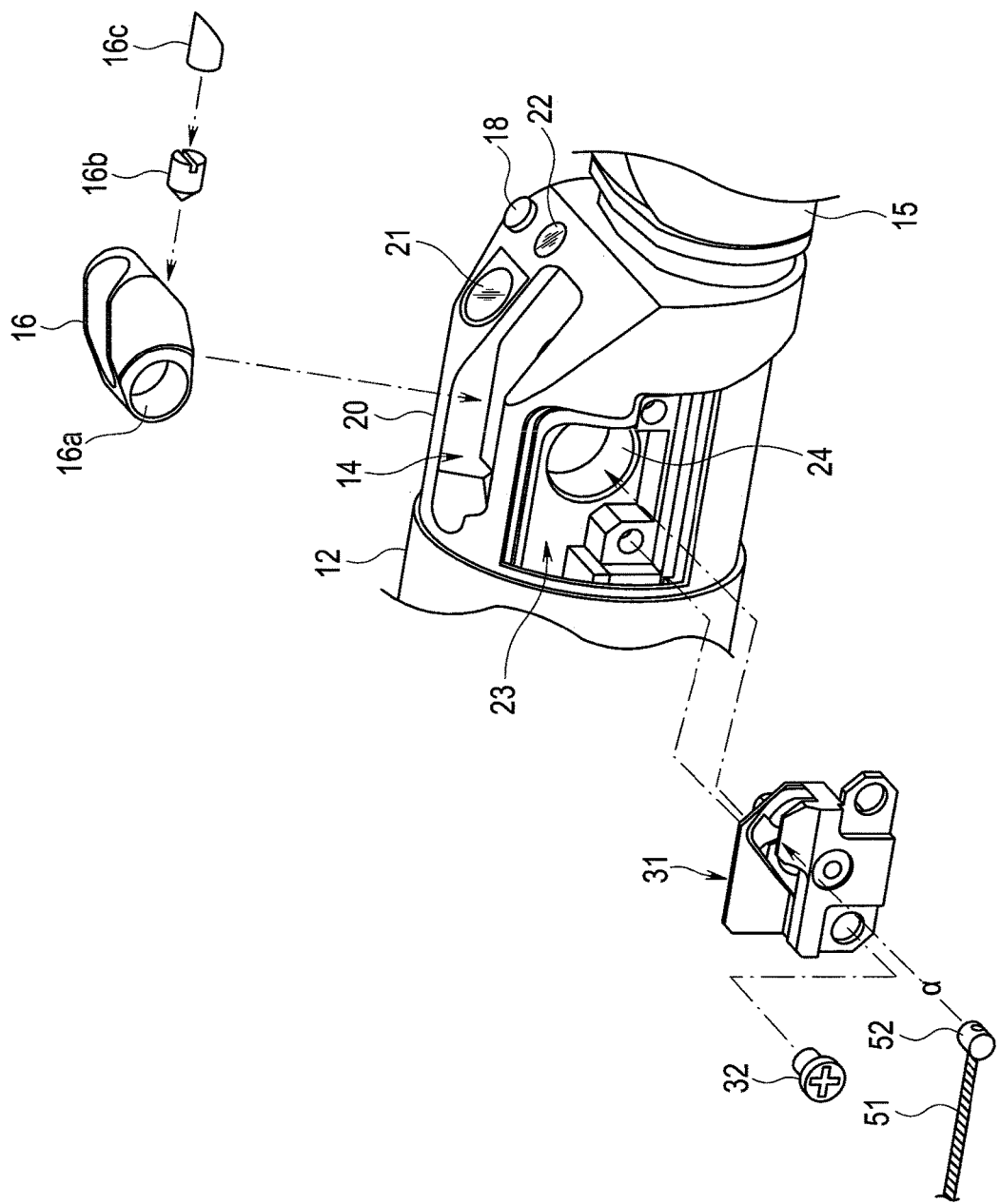
FIG. 3 is an exploded perspective view partially illustrating the configuration of the distal end portion.

As illustrated in FIG. 3, the distal end rigid portion 20 is provided with a raising-base rotation mechanism 31 configured to rotate the treatment instrument raising base 16. The raising-base rotation mechanism 31 is engaged with a wire lock portion 52 as a connection member at a distal end attachment-detachment portion of an operation wire 51 as a pulling wire.

The raising-base rotation mechanism 31 is fixed by a screw 32 to a recessed part 23 formed at a side surface of the distal end rigid portion 20. In this case, a rotation shaft 35 (refer to FIG. 4) of the raising-base rotation mechanism 31 is inserted into a through-hole 24 of the distal end rigid portion 20. Note that the through-hole 24 of the distal end rigid portion 20 communicates with the opening 14.

The rotation shaft 35 inserted in the through-hole 24 is inserted into a shaft hole 16a of the treatment instrument raising base 16 attached to the opening 14. A screw 16b is attached by screwing to a screw hole of the treatment instrument raising base 16 in this state. As a result, connection between the treatment instrument raising base 16 and the rotation shaft 35 is fixed. In addition, the screw hole of the treatment instrument raising base 16 is sealed by a screw hiding member 16c that is bonded and fixed.

Figure 4:
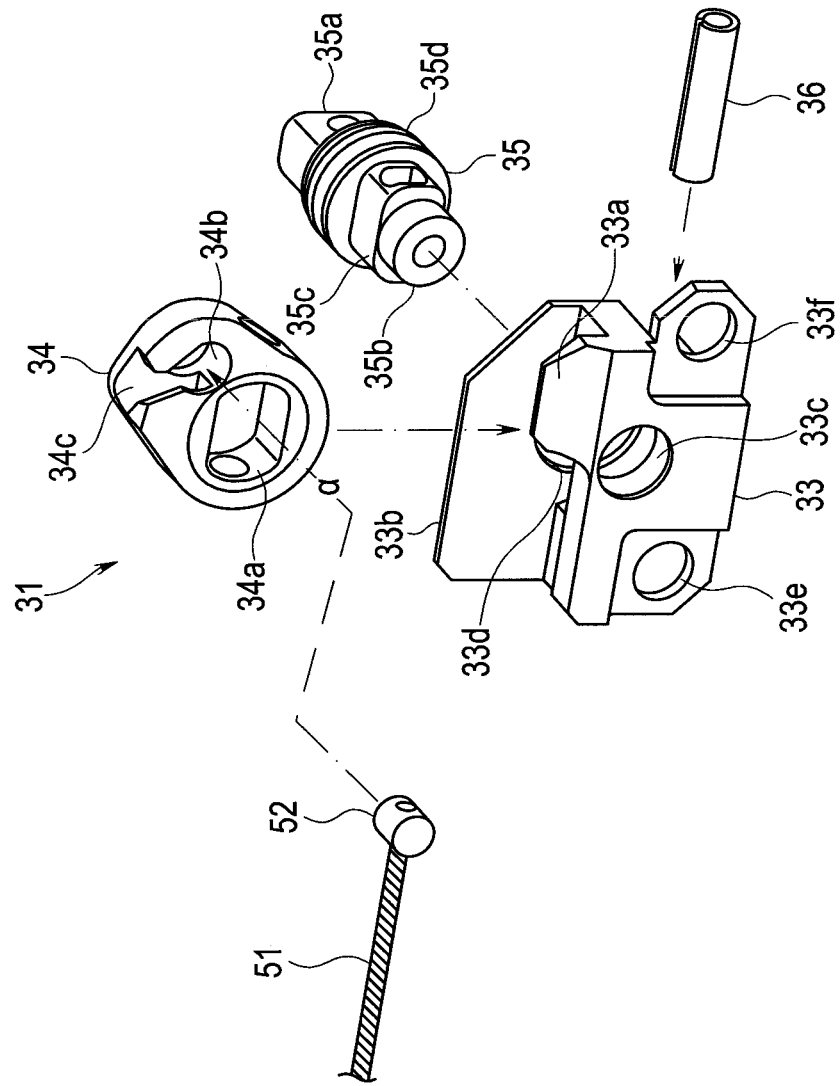
FIG. 4 is an exploded perspective view illustrating a configuration of a raising-base rotation mechanism.

As illustrated in FIG. 4, the raising-base rotation mechanism 31 includes a housing 33, an arm 34, and the rotation shaft 35.

The housing 33 rotatably supports the rotation shaft 35. The housing 33 includes a guide body 33a and a board body 33b. Two shaft holes 33c and 33d and two screw holes 33e and 33f are formed at the housing 33.

The guide body 33a is a plate member extending upward on the distal end side of the housing 33. The guide body 33a guides the arm 34 that rotates. In addition, the guide body 33a is configured as a removal prevention member that prevents removal of the wire lock portion 52 of the operation wire 51 connected to the arm 34 when the arm 34 rotates and moves to the distal end side and the treatment instrument raising base 16 is in a laid state.

The board body 33b is a plate member that planarly contacts a wall surface of the recessed part 23 of the distal end rigid portion 20 and stabilizes the raising-base rotation mechanism 31. The housing 33 is formed of metal such as stainless steel or aluminum, or alloy.

A through-hole 34a into which the rotation shaft 35 is inserted is formed at the arm 34. The through-hole 34a extends in a direction orthogonal to a longitudinal axis. A wire engagement hole 34b as a wire connection portion engaged with the cylindrical wire lock portion 52 provided at a distal end of the operation wire 51 is formed at the arm 34.

A slit 34c in which a distal end part of the operation wire 51 is disposed is formed at the arm 34. The slit 34c is formed to be continuous with the wire engagement hole 34b. The arm 34 is formed of metal such as stainless steel or aluminum, or alloy.

The rotation shaft 35 includes a raising-base connection body 35a, a small-diameter shaft body 35b, an arm connection body 35c, and a large-diameter shaft body 35d.

The raising-base connection body 35a is inserted into the shaft hole 16a of the treatment instrument raising base 16. The small-diameter shaft body 35b is rotatably engaged with the shaft hole 33c of the housing 33 on one side. The arm connection body 35c is engaged with the through-hole 34a of the arm 34. The large-diameter shaft body 35d is rotatably engaged with the shaft hole 33d of the housing 33 on the other side.

Note that the large-diameter shaft body 35d is provided with a seal member for watertight holding. The rotation shaft 35 is formed of metal such as stainless steel or aluminum, or alloy.

The arm 34 and the rotation shaft 35 are fixed to each other by insertion of a spring pin 36. Note that the arm 34 is disposed between the guide body 33a and the board body 33b of the housing 33.

In this case, the rotation shaft 35 is engaged with the through-hole 34a of the arm 34 after the small-diameter shaft body 35b is inserted into the shaft hole 33d of the housing 33. Then, the small-diameter shaft body 35b of the rotation shaft 35 is engaged with the one shaft hole 33c of the housing 33, and the large-diameter shaft body 35d of the rotation shaft 35 is engaged with the other shaft hole 33d.

Figure 5:
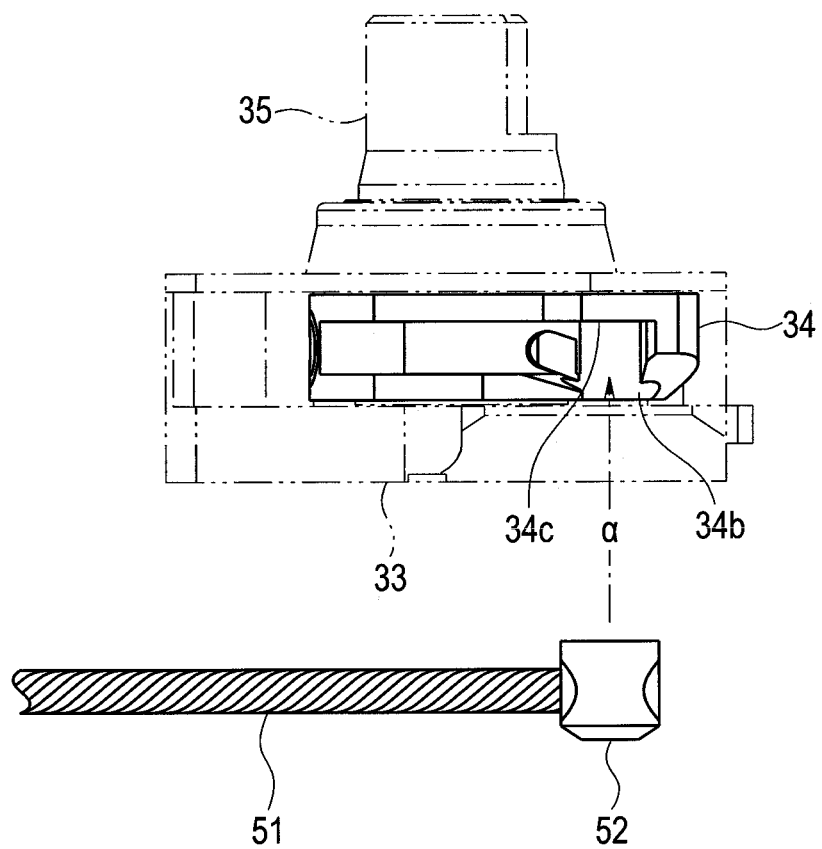
FIG. 5 is a diagram illustrating a direction in which an operation wire is attached to an arm.

Note that, as illustrated in FIGS. 3 to 5, in the operation wire 51, the wire lock portion 52 provided at the distal end is engaged with the wire engagement hole 34b from a side (attaching direction illustrated with arrow a) of the arm 34 in a direction orthogonal to the longitudinal axis. In other words, the operation wire 51 has a defined attaching direction to the arm 34.

Figure 6:
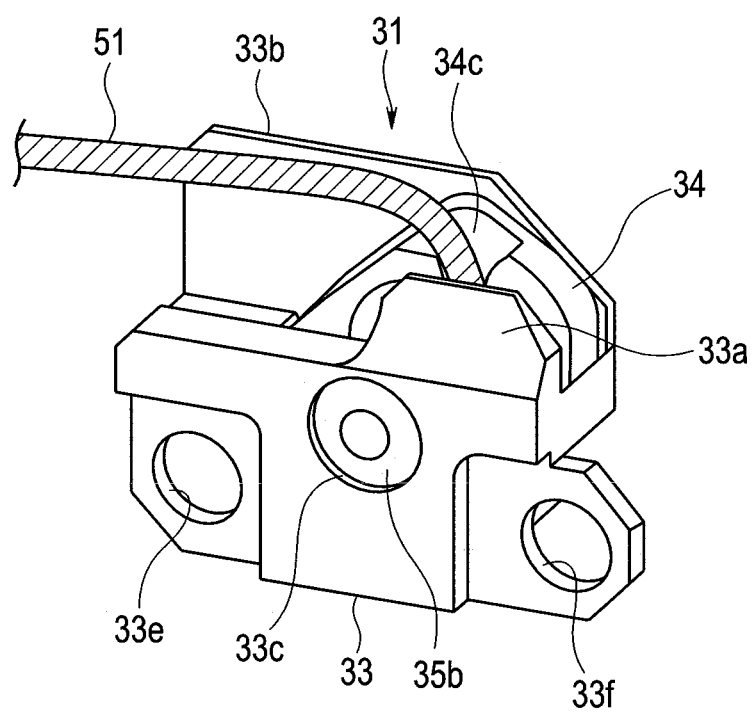
FIG. 6 is a perspective view illustrating the configuration of the raising-base rotation mechanism.

In this manner, the raising-base rotation mechanism 31 is assembled in a state in which the operation wire 51 is connected to the arm 34 as illustrated in FIG. 6. Note that the operation wire 51 is inserted into the insertion portion 2 of the endoscope 1 from the proximal end.

Figure 7:
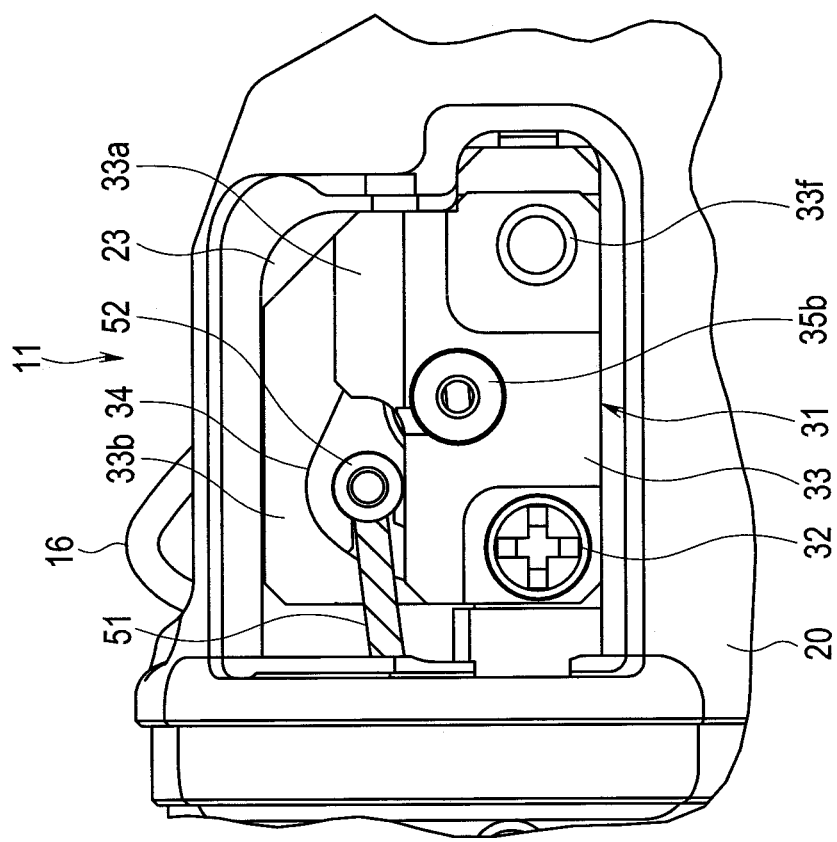
FIG. 7 is a side view partially illustrating a distal end rigid portion when viewed from the raising-base rotation mechanism side.

Then, as illustrated in FIGS. 3 and 7, the raising-base rotation mechanism 31 is fixed by the screw 32 to the recessed part 23 formed at the side surface of the distal end rigid portion 20. In this case, the treatment instrument raising base 16 is inserted inside through the opening 14 of the distal end rigid portion 20, fixed to the raising-base connection body 35a of the rotation shaft 35 by the screw 16b, and sealed by the screw hiding member 16c.

Figure 8:
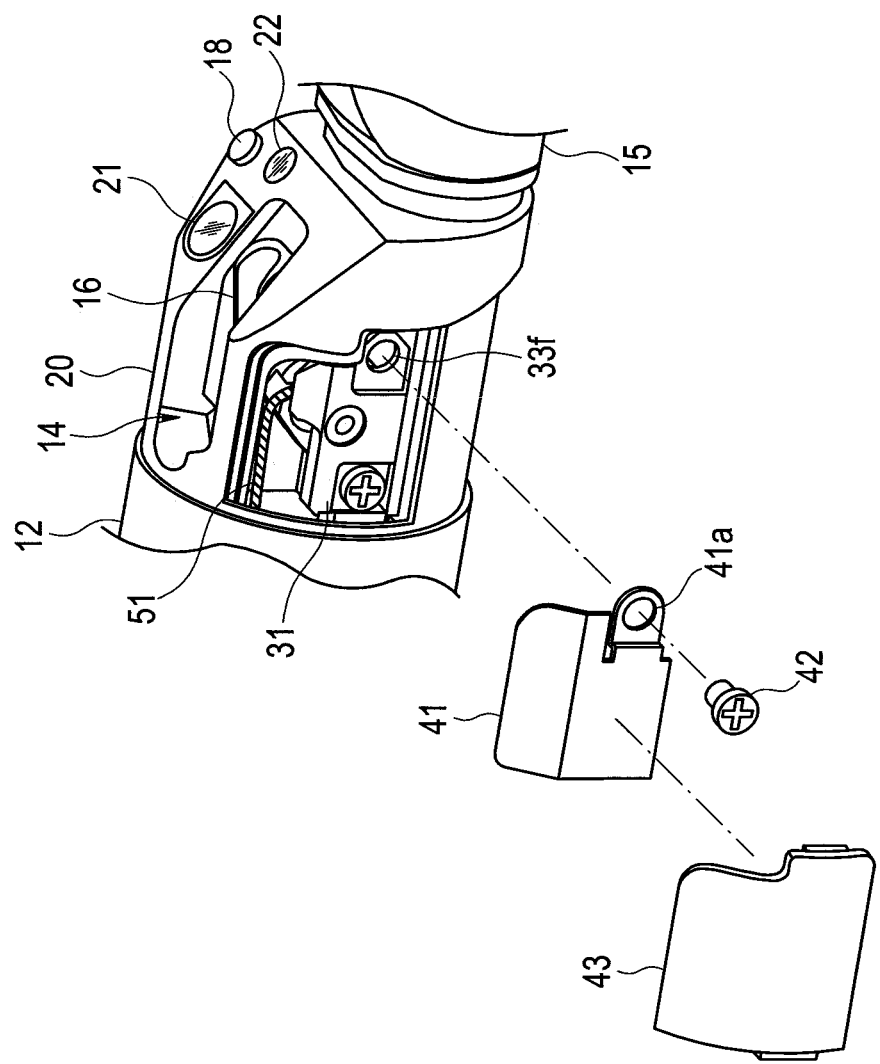
FIG. 8 is an exploded perspective view partially illustrating a state in which a cover and a lid body are attached to the distal end rigid portion.

Lastly, as illustrated in FIG. 8, a cover 41 is bonded by a bonding agent or the like to cover the recessed part 23 of the distal end rigid portion 20. Then, the cover 41 is screwed to the distal end rigid portion 20 as a screw 42 is inserted into a screw hole 41a of the cover 41 and a screw hole 33f of the raising-base rotation mechanism 31.

In addition, a lid body 43 is bonded to the distal end rigid portion 20 from above the cover 41 by a bonding agent. In this manner, the distal end portion 11 of the endoscope 1 is assembled.

Note that the operation wire 51 is extended on the proximal end side in the insertion portion 2 and moves forward and backward in an insertion direction in accordance with an operation of the operation lever 7 provided to the operation portion 3. The treatment instrument raising base 16 rotates and is raised and laid as the arm 34 and the rotation shaft 35 of the raising-base rotation mechanism 31 rotate in accordance with a forward-backward movement operation of the operation wire 51.

Description below is made on operation that the treatment instrument raising base 16 as a movable member provided to the endoscope 1 becomes a laid state or a raised state.

Figure 9:
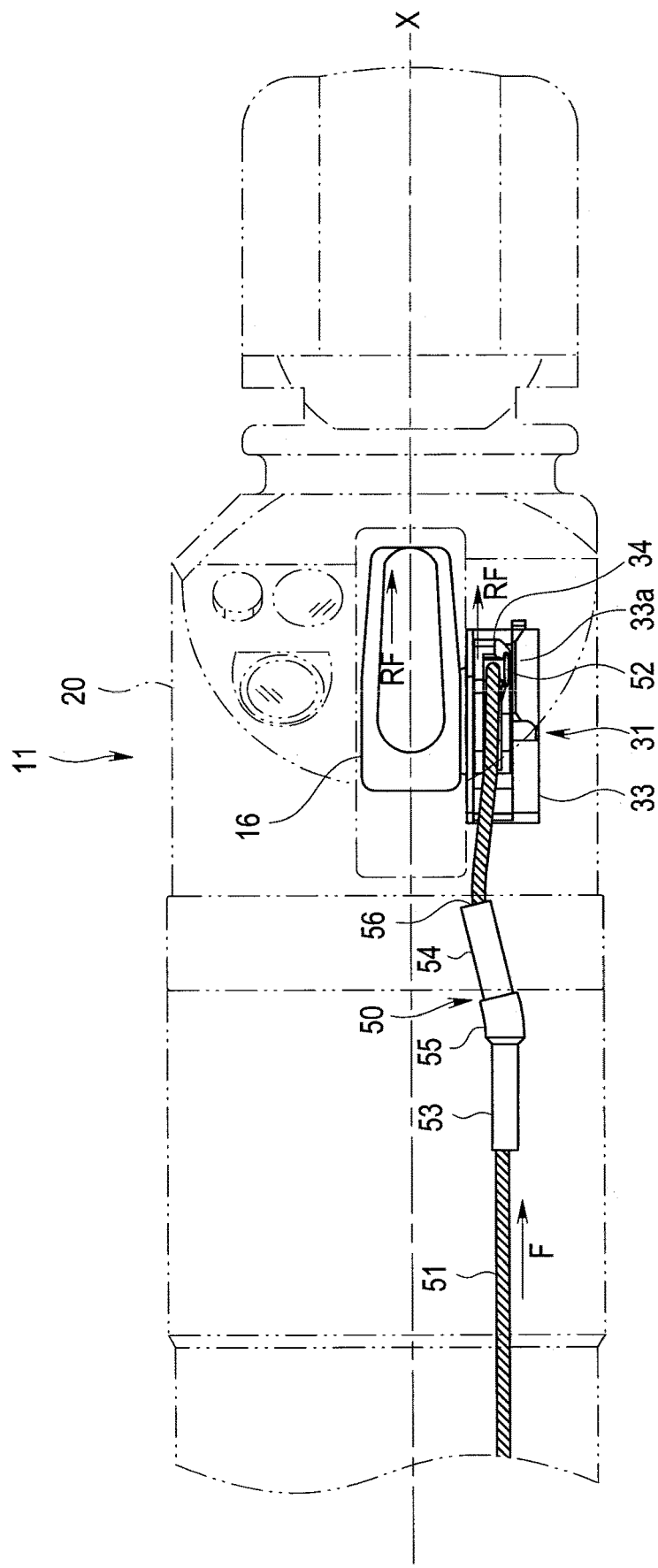
FIG. 9 is a top view illustrating the distal end portion in a state in which a treatment instrument raising base is laid.

As illustrated in FIG. 9, the treatment instrument raising base 16 becomes the laid state as the endoscope 1 becomes a loosened state in which the operation wire 51 is moved to the distal end side of the insertion portion 2 (arrow F in the drawing) based on an operation on the operation lever 7 of the operation portion 3. Note that the treatment instrument raising base 16 is in the laid state as a normal initial state of the endoscope 1.

In the laid state of the treatment instrument raising base 16, the arm 34 of the raising-base rotation mechanism 31 is pushed toward the distal end side by the operation wire 51 and rotated in an arrow RF direction in the drawing. Accordingly, the treatment instrument raising base 16 becomes inclined on the distal end side in the arrow RF direction in the drawing as the rotation shaft 35 connected to the arm 34 cooperatively rotates.

In this state, the arm 34 is at a position overlapping the guide body 33a of the housing 33, and the guide body 33a prevents the wire lock portion 52 of the operation wire 51 from being removed from the wire engagement hole 34b of the arm 34.

Figure 10:
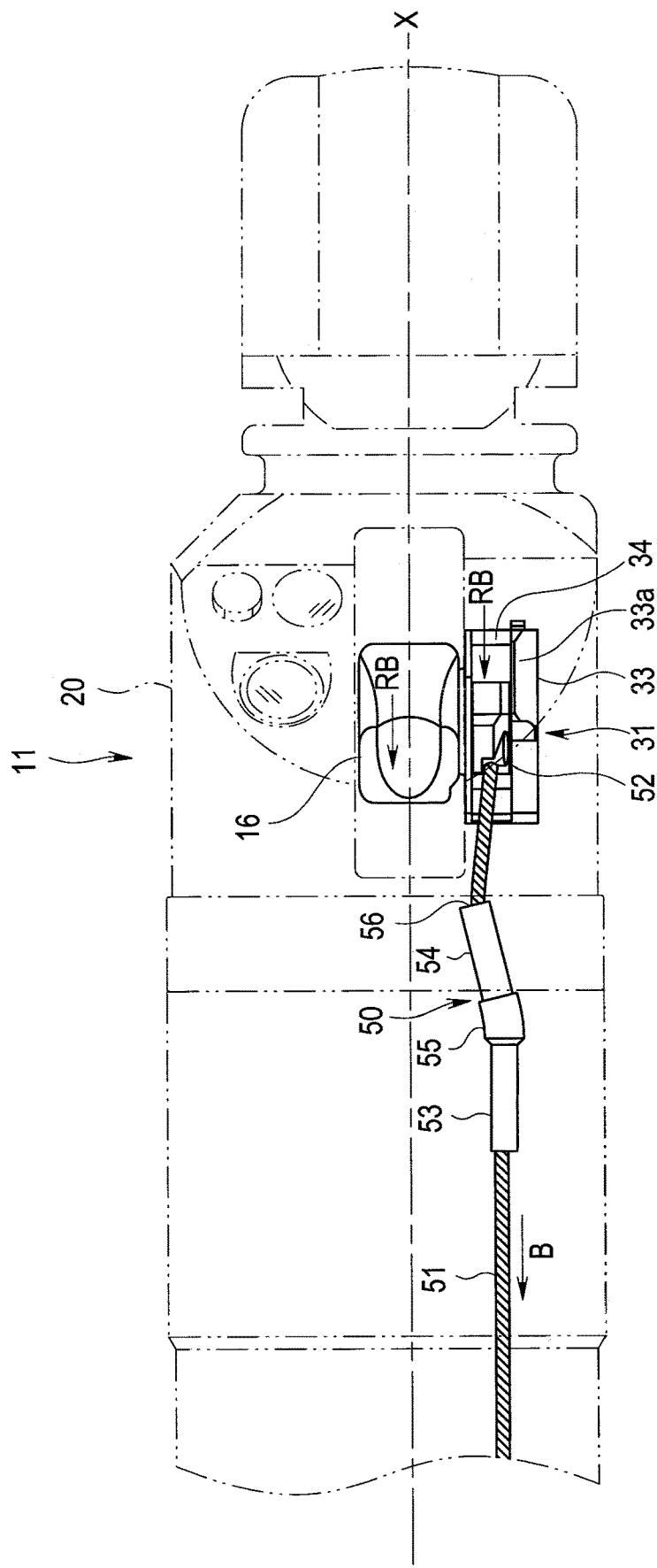
FIG. 10 is a top view illustrating the distal end portion in a state in which the treatment instrument raising base is raised.

As illustrated in FIG. 10, the treatment instrument raising base 16 becomes the raised state as the endoscope 1 becomes a pulled state in which the operation wire 51 is moved on the proximal end side of the insertion portion 2 (arrow B in the drawing) based on an operation on the operation lever 7 of the operation portion 3.

In the raised state of the treatment instrument raising base 16, the arm 34 of the raising-base rotation mechanism 31 is pulled to the proximal end side by the operation wire 51 and rotated in an arrow RB direction in the drawing. Accordingly, the treatment instrument raising base 16 becomes raised on the proximal end side in the arrow RB direction in the drawing as the rotation shaft 35 connected to the arm 34 cooperatively rotates.

A metal pipe 50 as a rigid guide is disposed in the distal end rigid portion 20. The operation wire 51 is inserted into the metal pipe 50 to be freely movable forward and backward.

Figure 11:
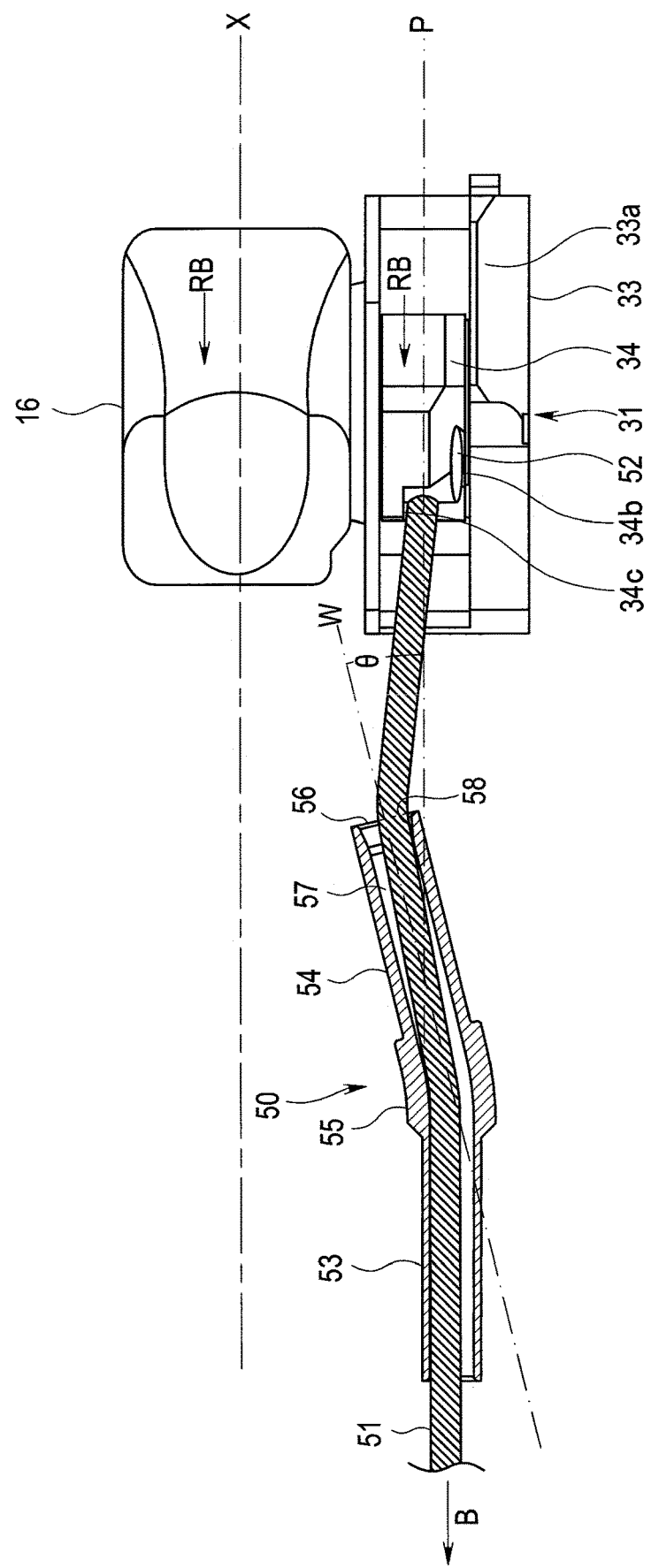
FIG. 11 is a schematic explanatory diagram illustrating a section of a metal pipe in the state in which the treatment instrument raising base is raised.

As illustrated in FIG. 11, the metal pipe 50 is a V-shaped pipeline member including a curved portion 55 so that a distal end pipe 54 is on an inner side of the distal end rigid portion 20 relative to a proximal end pipe 53. The metal pipe 50 has a wire insertion path 57 as a pipeline into which the operation wire 51 is inserted.

A taper 58 in which a pipeline diameter decreases from a distal end opening 56 toward inside of the wire insertion path 57 is formed at the metal pipe 50. Thus, the taper 58 on an inner peripheral surface of the distal end opening 56 of the metal pipe 50 reduces damage on the operation wire 51 due to, for example, friction at forward and backward movement by pulling and loosening. The metal pipe 50 is formed of metal such as stainless steel or aluminum, or alloy.

An inner peripheral surface of the metal pipe 50 (including the inner peripheral surface of the distal end opening 56) may be coated with lubrication material such as fluorine resin to further reduce friction on the operation wire 51. The same effect can be obtained by coating an outer surface of the operation wire 51 with lubrication material such as fluorine resin.

The metal pipe 50 is disposed in the distal end rigid portion 20 so that the distal end opening 56 is positioned on the proximal end side of the arm 34 of the raising-base rotation mechanism 31 as a movable member and the treatment instrument raising base 16. The proximal end pipe 53 of the metal pipe 50 is positioned in a side peripheral portion direction farther away from a central axis X of the distal end rigid portion 20 in a longitudinal direction than the distal end opening 56 of the distal end pipe 54.

Specifically, to prevent interference with an internal component of the bending portion 12, in the metal pipe 50, the operation wire 51 is disposed on an outer peripheral side in the bending portion 12 as much as possible on the proximal end side of the distal end rigid portion 20 and the proximal end pipe 53 is disposed in the side peripheral portion direction farther away from the central axis X of the distal end rigid portion 20 in the longitudinal direction than the distal end pipe 54.

In the metal pipe 50, the distal end pipe 54 is disposed so that the distal end opening 56 of the distal end pipe 54 is located at a position closer to the central axis X of the distal end rigid portion 20 in the longitudinal direction than a position in a plane P formed by a rotation trajectory of the wire lock portion 52 of the operation wire 51 engaged with the arm 34 of the raising-base rotation mechanism 31 as a movable member.

Thus, the metal pipe 50 includes the curved portion 55 at which the proximal end pipe 53 and the distal end pipe 54 form a V shape at a certain angle. Since the metal pipe 50 is a bent pipe provided with the curved portion 55 in this manner, the proximal end pipe 53 is disposed on an outer side of the distal end rigid portion 20, and the distal end pipe 54 is disposed on an inner side of the distal end rigid portion 20.

Note that the metal pipe 50 is disposed in the distal end rigid portion 20 so that a hole axis W of the distal end pipe 54 has a certain angle θ relative to the plane P of the rotation trajectory of the wire lock portion 52 connected to the arm 34. A bent angle of the metal pipe 50 due to the curved portion 55 is set as appropriate in accordance with a form of avoiding interference with an internal object.

In the endoscope 1 configured as described above, the wire lock portion 52 moving in accordance with rotation of the arm 34 is pulled in an oblique direction toward the central axis X. Specifically, as the operation wire 51 is pulled in the arrow B direction to raise the treatment instrument raising base 16, the wire lock portion 52 is pulled toward the central axis X on the proximal end side since the distal end opening 56 of the metal pipe 50 is positioned on a side closer to the central axis X of the distal end rigid portion 20 than the rotation trajectory (plane P) of the wire lock portion 52 engaged with the arm 34.

Figure 12:
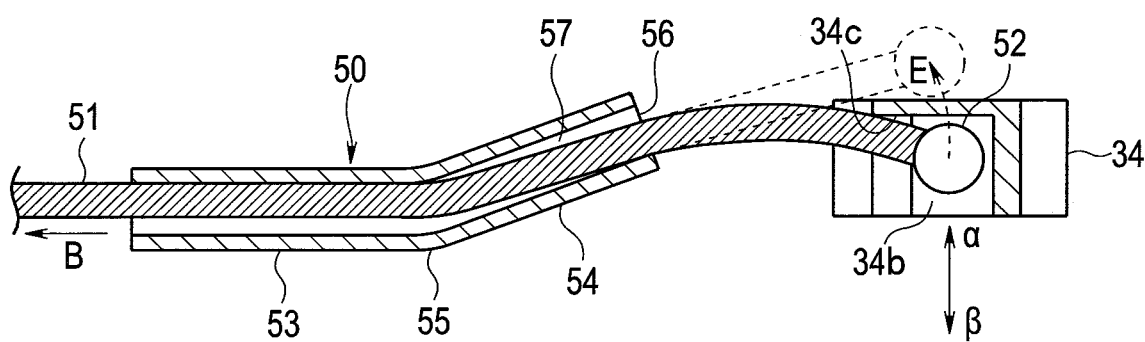
FIG. 12 is a cross-sectional view for description of a stress component generated at a wire lock portion of the operation wire.

In this case, as illustrated in FIG. 12, a component of stress E in the attaching direction α to the wire engagement hole 34b of the arm 34 is generated at the wire lock portion 52. In other words, as the operation wire 51 is pulled, a component of force (stress E) in the attaching direction α opposite to a detaching direction θ of removal from the wire engagement hole 34b of the arm 34 acts on the wire lock portion 52.

Thus, a component of force (stress E) to the treatment instrument raising base 16 as a movable member toward the central axis X of the distal end rigid portion 20 contacting a wall surface of the wire engagement hole 34b of the arm 34 acts on the wire lock portion 52 as a connection member that connects the operation wire 51 to the arm 34. Accordingly, the wire lock portion 52 is prevented from being removed from the wire engagement hole 34b of the arm 34.

In this manner, the endoscope 1 according to the present embodiment has a configuration in which the metal pipe 50 is disposed in the distal end rigid portion 20 at a position to prevent the wire lock portion 52 from being removed from the wire engagement hole 34b of the arm 34 at pulling of the operation wire 51 to raise the treatment instrument raising base 16.

The endoscope 1 also has a configuration in which the curved portion 55 that sets the distal end pipe 54 as appropriate at a certain angle relative to the proximal end pipe 53 of the metal pipe 50 is provided to avoid interference of the operation wire 51 extending from the proximal end pipe 53 with another internal object.

As described above, when the operation wire 51 as a pulling member is pulled backward to raise the treatment instrument raising base 16 as a movable member, the endoscope 1 can generate a tension component at the operation wire 51 in the inner side direction of the distal end rigid portion 20, thereby preventing the operation wire 51 from coming off the arm 34.

Thus, the treatment instrument raising base 16 does not receive impact at raising and is prevented from suffering backlash. Accordingly, the treatment instrument raising base 16 can prevent occurrence of a defect such as an insufficient raising angle of a treatment instrument.

The endoscope 1 described above has a configuration that can prevent removal from the raising-base rotation mechanism 31, which raises the treatment instrument raising base 16 as a movable member, due to impact at pulling of the operation wire 51, and solve a defect such as backlash.

Note that the present embodiment exemplarily describes a configuration in which the wire lock portion 52 of the operation wire 51 is connected to the arm 34 of the raising-base rotation mechanism 31, but is not limited to the configuration and is also applicable to a configuration in which the wire lock portion 52 is directly connected to the treatment instrument raising base 16.

The movable member in a detachment prevention structure of the operation wire 51 is not limited to the treatment instrument raising base 16 nor the arm 34 but is also applicable to various kinds of components that can move as the operation wire 51 is pulled and loosened.

The endoscope 1 is assembled when the treatment instrument raising base 16 as one movable member is rotatably held to the distal end rigid portion 20 as a frame member, the wire lock portion 52 as a connection member of the operation wire 51 as a pulling wire that rotates the arm 34 of the raising-base rotation mechanism 31 as one movable member is engaged with the wire connection portion of the arm 34, the distal end opening 56 of the wire insertion path 57 of the metal pipe 50 as a rigid guide that guides the operation wire 51 is disposed on the proximal end side of the treatment instrument raising base 16 and the arm 34, and positioning is performed so that the distal end opening 56 of the wire insertion path 57 of the metal pipe 50 is disposed at a position close to the central axis X of the distal end rigid portion 20 in the longitudinal axis than a position in the plane P formed by the rotation trajectory of the wire lock portion 52 rotating along with rotation of the treatment instrument raising base 16 and the arm 34.

(Modification)

Figure 13:
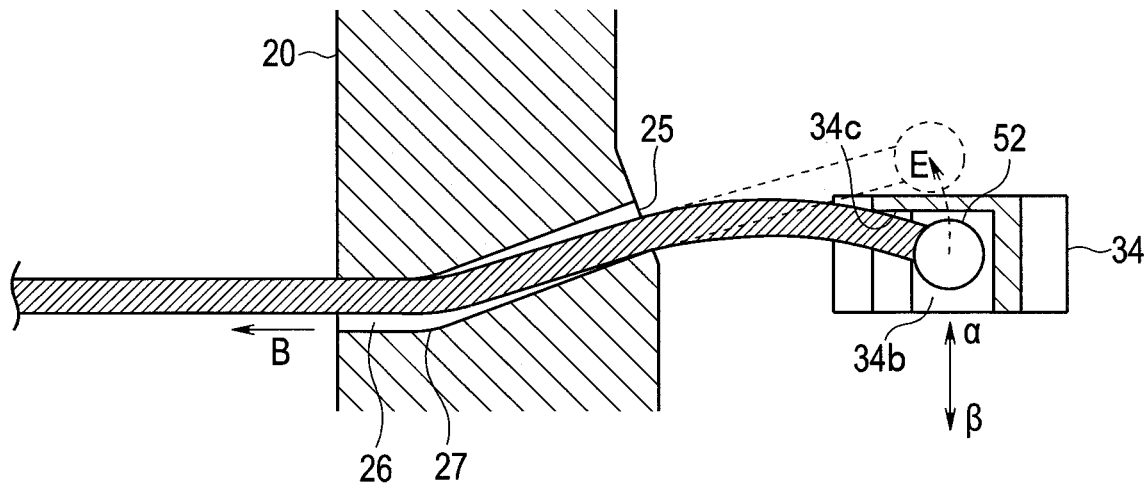
FIG. 13 is a cross-sectional view for description of a stress component generated at the wire lock portion of the operation wire in a configuration in which a wire insertion path is formed at the distal end rigid portion in place of the metal pipe according to a modification.

In the above-described embodiment, the metal pipe 50 is provided in the distal end rigid portion 20, but a wire insertion path 26 may be formed in the distal end rigid portion 20 as a frame member as illustrated in FIG. 13. Note that the wire insertion path 26 has a V shape in which a curved portion 27 is formed, and a distal end opening 25 is formed on a side closer to the central axis X of the distal end rigid portion 20 than the rotation trajectory (the plane P) of the wire lock portion 52 engaged with the arm 34.

Reference Example

Figure 14:
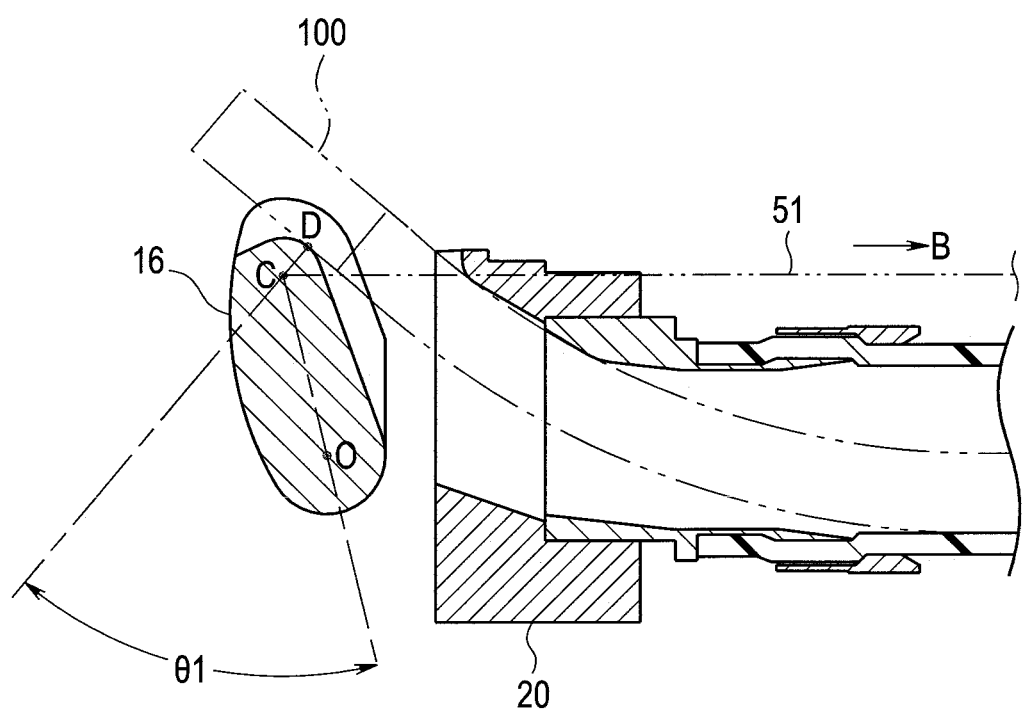
FIG. 14 is a cross-sectional view in a state in which a treatment instrument raising base is raised according to a reference example.

As illustrated in FIG. 14, the treatment instrument raising base 16 provided to the endoscope 1 is rotated and raised to sandwich the treatment instrument 100 between a contact part with the treatment instrument 100 and an upper part of a channel opening of the distal end component 20 or the like, thereby bending and raising the treatment instrument 100 at maximum.

It is desired for such a mechanism of the treatment instrument raising base 16 of the endoscope 1 to increase an angle at which the treatment instrument raising base 16 is caused to raise the treatment instrument 100 by a user and reduce an amount of force with which the treatment instrument raising base 16 raises the treatment instrument 100 (force of pulling the operation wire 51).

A movable range of the treatment instrument 100 increases as the angle at which the treatment instrument raising base 16 raises the treatment instrument 100 at maximum increases. In addition, a load on the user can be reduced as the amount of force when the treatment instrument raising base 16 raises the treatment instrument 100 at maximum is reduced.

In FIG. 14, an angle θ1 between a line segment connecting a rotation center O of the treatment instrument raising base 16 and a connection point C of the operation wire 51 and a line segment connecting the connection point C and a contact point D of the treatment instrument raising base 16 and the treatment instrument 100 is large, and the connection point C and the contact point D are positioned on the distal end side of the rotation center O.

In this state, an amount of force that pulls the operation wire 51 in a proximal end direction (arrow B direction) is large. Specifically, the treatment instrument raising base 16 receives reaction force in accordance with restoring force with which the treatment instrument 100 becomes straight, and thus when the rotation center O is positioned on the proximal end side of the contact point D, rotation moment (rotation torque) toward the distal end side is generated due to the principle of leverage. Accordingly, certain pulling force against tension of the operation wire 51 is needed to maintain a state in which the treatment instrument 100 is raised at maximum.

Figure 15:
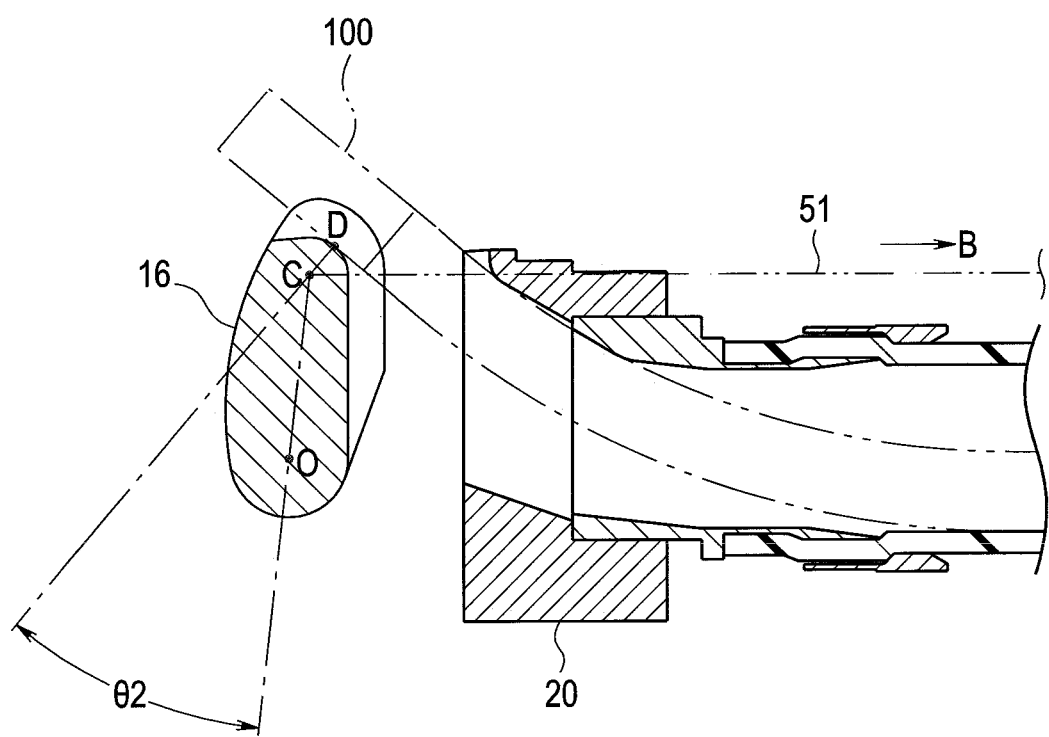
FIG. 15 is a cross-sectional view of a raised state of the treatment instrument raising base with reduced force that pulls the operation wire according to the reference example.

Thus, as illustrated in FIG. 15, the mechanism of the treatment instrument raising base 16 is set to a state in which the line segment connecting the rotation center O of the treatment instrument raising base 16 and the connection point C of the operation wire 51 and the line segment connecting the connection point C and the contact point D of the treatment instrument raising base 16 and the treatment instrument 100 have a small angle θ2 and the connection point C and the contact point D are positioned on the proximal end side of the rotation center O.

With this state, the amount of force that pulls the operation wire 51 in the proximal end direction (arrow B direction) can be reduced. Specifically, rotation moment (rotation torque) toward the distal end side on the treatment instrument raising base 16 can be reduced when the rotation center O is positioned on the proximal end side of the contact point D. Thus, it is possible to reduce certain pulling force against tension of the operation wire 51 to maintain the state in which the treatment instrument 100 is raised at maximum. Thus, the amount of force that pulls the operation wire 51 can be reduced for the same raising angle.

Thus, the treatment instrument raising base 16 can be raised at a larger angle with a conventional amount of force that pulls the operation wire 51.

Specifically, reaction force to bending of the treatment instrument 100 is generated at the contact point D of the treatment instrument raising base 16 contacting the treatment instrument 100, and force that pulls the operation wire 51 needs to be sufficient to generate rotation torque of the treatment instrument raising base 16 against the reaction force.

The rotation torque against the reaction force is smaller with the smaller angle θ2 in FIG. 15 than the angle 1 in FIG. 14. Thus, when the contact point D of the treatment instrument raising base 16 and the treatment instrument 100 is positioned on the proximal end side of the rotation center O of the treatment instrument raising base 16, rotation torque generated at the treatment instrument raising base 16 by reaction force from the treatment instrument 100 is reduced and the force that pulls the operation wire 51 is reduced, which can reduce a load on the user.

Note that the above-described technology of the endoscope 1 is applicable to either of a reuse endoscope and a single-use endoscope.

The invention described above in the embodiment and modification is not limited to the embodiment and the modification but may include various kinds of other modifications without departing from the gist of the invention when performed. Moreover, inventions at various kinds of stages are included in the above-described embodiment and modification, and various kinds of inventions can be extracted with appropriate combinations among a plurality of disclosed components.

For example, some components may be deleted from among all components described in the embodiment and the modification, and a configuration from which the components are deleted may be extracted as an invention as long as a described problem can be solved and described effects can be obtained.

What is claimed is:
1. An endoscope comprising:
a distal end portion of an insertion portion;
a movable member rotatably connected to the distal end portion of the insertion portion;
a wire connected to the movable member and configured to rotate the movable member; and
a rigid guide channel configured to receive the wire, the guide channel being located proximally relative to the movable member;
wherein, as the guide channel extends distally, at least a distal-most portion of the guide channel is inclined inwardly toward a longitudinal axis of the distal end portion of the insertion section; and the guide channel is configured to maintain the inclination when the wire is tensioned to rotate the movable member.

2. The endoscope according to claim 1, wherein the movable member comprises a treatment instrument raising base,
wherein the movable member being an arm configured to rotate the treatment instrument raising base; and
the movable member having a wire connection portion for connecting the wire to the movable member.

3. The endoscope according to claim 2, wherein the wire comprising a connection member provided at a distal end of the wire, the connection member being engaged with the wire connection portion of the movable member, an attaching and detaching direction of the connection member being orthogonal to a center axis along a longitudinal direction of the distal end portion of the insertion section.

4. The endoscope according to claim 3, wherein a distal opening of the distal-most portion of the guide channel is disposed closer to t center axis of the insertion portion than the connection portion.

5. The endoscope according to claim 1, wherein the guide channel is a metal pipe.

6. The endoscope according to claim 1, wherein the guide channel includes a curved portion located proximally relative to the distal-most portion of the guide channel.

7. The endoscope according to claim 6, wherein the guide channel is a metal pipe; and
a proximal end side of the guide channel is positioned farther away from a center axis than the distal-most portion of the guide channel.

8. The endoscope according to claim 1, wherein the distal-most portion of the guide channel having a hole for receiving the wire.

9. The endoscope according to claim 1, wherein:
the wire comprising a connection member provided at a distal end of the wire, the connection member being engaged with a wire connection portion of the movable member, an attaching and detaching direction of the connection member with the wire connection portion being orthogonal to a center axis along a longitudinal direction of the distal end portion of the insertion section; and
tension generated at the wire when the wire is pulled has a component that pushes the connection member toward the center axis.

10. The endoscope according to claim 1, wherein the guide channel comprising a tapered portion disposed on an inner circumferential surface of the distal-most portion of the guide channel.

11. A method of manufacturing an endoscope, the method comprising:
rotatably connecting a movable member to a distal end portion of an insertion portion;
engaging a wire with the movable member, the wire being configured to rotate the movable member;
arranging a distal-most portion of a rigid guide channel on a proximal end side relative to the movable member, the guide channel being configured to receive the wire; and
positioning at least the distal-most portion of the guide channel to incline inwardly toward a longitudinal axis of the distal end portion of the insertion section, as the guide channel extends distally;
wherein the guide channel is configured to maintain the inclination when the wire is tensioned to rotate the movable member.

12. The endoscope according to claim 1, wherein the guide channel is a rigid guide pipe, the guide pipe comprising:
a rigid distal pipe, and
a rigid proximal pipe inclined relative to the distal pipe.

13. The endoscope according to claim 12, wherein the guide pipe comprising a transition portion located between the distal pipe and the proximal pipe.

14. The endoscope according to claim 13, wherein the transition portion is curved.

15. The endoscope according to claim 14, wherein a diameter of the curve of the transition portion is larger than a diameter of the distal pipe and larger than a diameter of the proximal pipe.

16. An endoscope comprising:
a distal end portion of an insertion portion;
a movable member rotatably connected to the distal end portion of the insertion portion;
a wire connected to the movable member at a connection portion, the wire being configured to rotate the movable member when the wire is tensioned; and
a guide channel configured to receive the wire, the guide channel being located proximally relative to the movable member;
wherein a distal opening of a distal-most portion of the guide channel is disposed at a position closer to a center axis of the insertion portion than the connection portion, and
the distal opening of the distal-most portion of the guide channel is configured to maintain the position when the wire is tensioned to rotate the movable member.

17. The endoscope according to claim 16, wherein a proximal end side of the guide channel is positioned farther away from the center axis than the distal-most portion of the guide channel.

18. The endoscope according to claim 17, wherein the guide channel is a guide pipe, the guide pipe comprising:
a distal pipe, and
a proximal pipe inclined relative to the distal pipe.

19. The endoscope according to claim 18, wherein the guide pipe comprising a transition portion located between the distal pipe and the proximal pipe.

20. The endoscope according to claim 19, wherein the transition portion is curved.

* * * * *